(12) United States Patent
Wegmann

(10) Patent No.: US 10,213,998 B2
(45) Date of Patent: Feb. 26, 2019

(54) ASSEMBLY AND PROCESS FOR PREPARING AFFIXING TAPE

(71) Applicant: Mark Wegmann, Chesterfield, MO (US)

(72) Inventor: Mark Wegmann, Chesterfield, MO (US)

(*) Notice: Subject to any disclaimer, the term of this patent is extended or adjusted under 35 U.S.C. 154(b) by 240 days.

(21) Appl. No.: 15/140,685

(22) Filed: Apr. 28, 2016

(65) Prior Publication Data

US 2016/0325537 A1    Nov. 10, 2016

Related U.S. Application Data

(60) Provisional application No. 62/156,523, filed on May 4, 2015.

(51) Int. Cl.
| | |
|---|---|
| *B65H 39/14* | (2006.01) |
| *B26D 1/22* | (2006.01) |
| *B26F 1/38* | (2006.01) |
| *B32B 7/12* | (2006.01) |
| *B32B 37/00* | (2006.01) |
| *B32B 38/00* | (2006.01) |
| *B32B 38/18* | (2006.01) |

(52) U.S. Cl.
CPC ............ *B32B 37/025* (2013.01); *B26D 1/225* (2013.01); *B26F 1/384* (2013.01); *B32B 7/12* (2013.01); *B32B 38/0004* (2013.01); *B32B 38/185* (2013.01); *B32B 38/1858* (2013.01); *B32B 2405/00* (2013.01); *B65H 39/14* (2013.01); *B65H 2701/194* (2013.01); *Y10T 156/1077* (2015.01)

(58) Field of Classification Search
CPC .............. B65H 2701/194; B65H 39/14; B32B 38/185; Y10T 156/1077
USPC ........ 156/238, 265, 289, 297, 299, 302, 519, 156/543
See application file for complete search history.

(56) References Cited

U.S. PATENT DOCUMENTS

| | | | |
|---|---|---|---|
| 8,608,889 B2 * | 12/2013 | Sever ..................... | A61K 9/703 156/234 |
| 2006/0194412 A1 * | 8/2006 | Nakayama ........... | B65H 37/002 438/455 |

* cited by examiner

*Primary Examiner* — Carson Gross
(74) *Attorney, Agent, or Firm* — Armstrong Teasdale LLP

(57) ABSTRACT

This disclosure relates generally to an assembly and process for preparing affixing tape. The disclosure also relates to an affixing assembly and process using the prepared tape. The tape can be used, for example, to affix plastic items to mailing pieces. The assemblies and processes disclosed herein provide for added throughput, less down time, higher quality of parts and production control.

10 Claims, 5 Drawing Sheets

ASSEMBLY AND PROCESS FOR PREPARING AFFIXING TAPE

CROSS-REFERENCE TO RELATED APPLICATIONS

This application claims priority benefit of U.S. Provisional Patent Application No. 62/156,523, filed May 4, 2015, the entire contents and disclosure of which are hereby incorporated by reference in their entirety.

FIELD OF THE DISCLOSURE

This disclosure relates generally to an assembly and process for preparing affixing tape. The disclosure also relates to an affixing assembly and process using the prepared tape. The tape can be used, for example, to affix plastic items to mailing pieces. The assemblies and processes disclosed herein provide for added throughput, less down time, higher quality of parts and production control.

BACKGROUND OF THE DISCLOSURE

When plastic and/or other types of cards are affixed to, for example, mailing pieces and then mailed to consumers, some form of adhesive is generally used to affix the card to the mailing piece. This can be done, for example, in an automated fashion, and the card will stick to the mailing piece until it arrives to the intended consumer, who then removes the card and can discard the adhesive and the remainder of the mailing piece.

Previously used methods for affixing the cards to mailing pieces include using a "blob" of hot melt adhesive (or other liquid). Other methods include using a differential double-coated tape (DCT), also referred to as a "film tape". These DCTs have a high-tack adhesive on one side of a film or paper carrier to adhere to the mailing piece. These DCTs also have a low-tack adhesive on the other side of the film or paper carrier that removes cleanly from the card.

The DCT can be die-cut into a certain shape and then dispensed in a manner to speed the production of affixing the cards to the mailing pieces. There are limitations, however, to these methods. For example, there are limitations on the diameter of the tape (e.g., DCT) used, due to press limitations and handling issues. As a result, the finished product is produced in a limited length, which requires a number of roll changes during a worker's production shift. When a roll change occurs, the production machine almost always must stop, and this, in turn, costs the manufacturer money as a loss of production time. These losses can account for up to, for example, 15% or more of production time in a typical worker's shift.

Additionally, within the process of die-cutting the DCT, the tooling—especially during long runs when using hard base materials like films—will heat up and expand. When this occurs, the die will expand enough to cut deeper than required, which breaks through the release (e.g., silicone coating) on the release liner. This, in turn, allows the adhesive, over time and under certain circumstances, to flow into the same die-cut crevices and cause the parts to stick and not release from the liner as intended, or liner breakage causing failure within the affixing process. These failures can shut down production until new or "fresh" material arrives, which can cost the manufacturer a significant amount of money via lost production time.

A need exists, therefore, for an affixing assembly and process that overcomes the deficiencies of the prior art that will provide for added throughput, less down time, higher quality of parts and production control.

BRIEF DESCRIPTION OF THE DRAWINGS

Like reference symbols in the various drawings indicate like elements.

SUMMARY OF THE DISCLOSURE

In some embodiments of the present disclosure, an assembly is disclosed. The assembly comprises a cutting unit configured to cut a film tape at fixed intervals into pieces, and a transfer unit downstream from the cutting unit. The transfer unit is configured to transfer the film tape pieces from a first liner to a second liner.

In other embodiments of the present disclosure, a process is disclosed. The process comprises butt-cutting a film tape at regular intervals into pieces; and transferring the film tape pieces from a first liner to a second liner.

In still other embodiments of the present disclosure, a process is disclosed. The process comprises die-cutting a film tape at intervals into pieces; and transferring the film tape pieces from a first liner to a second liner.

DETAILED DESCRIPTION OF THE DISCLOSURE

The present disclosure describes an assembly and process for preparing affixing tape. The assembly comprises a cutting unit configured to cut a film tape at fixed intervals into pieces, and a transfer unit downstream from the cutting unit. The transfer unit is configured to transfer the film tape pieces from a first liner to a second liner.

Figure 1:
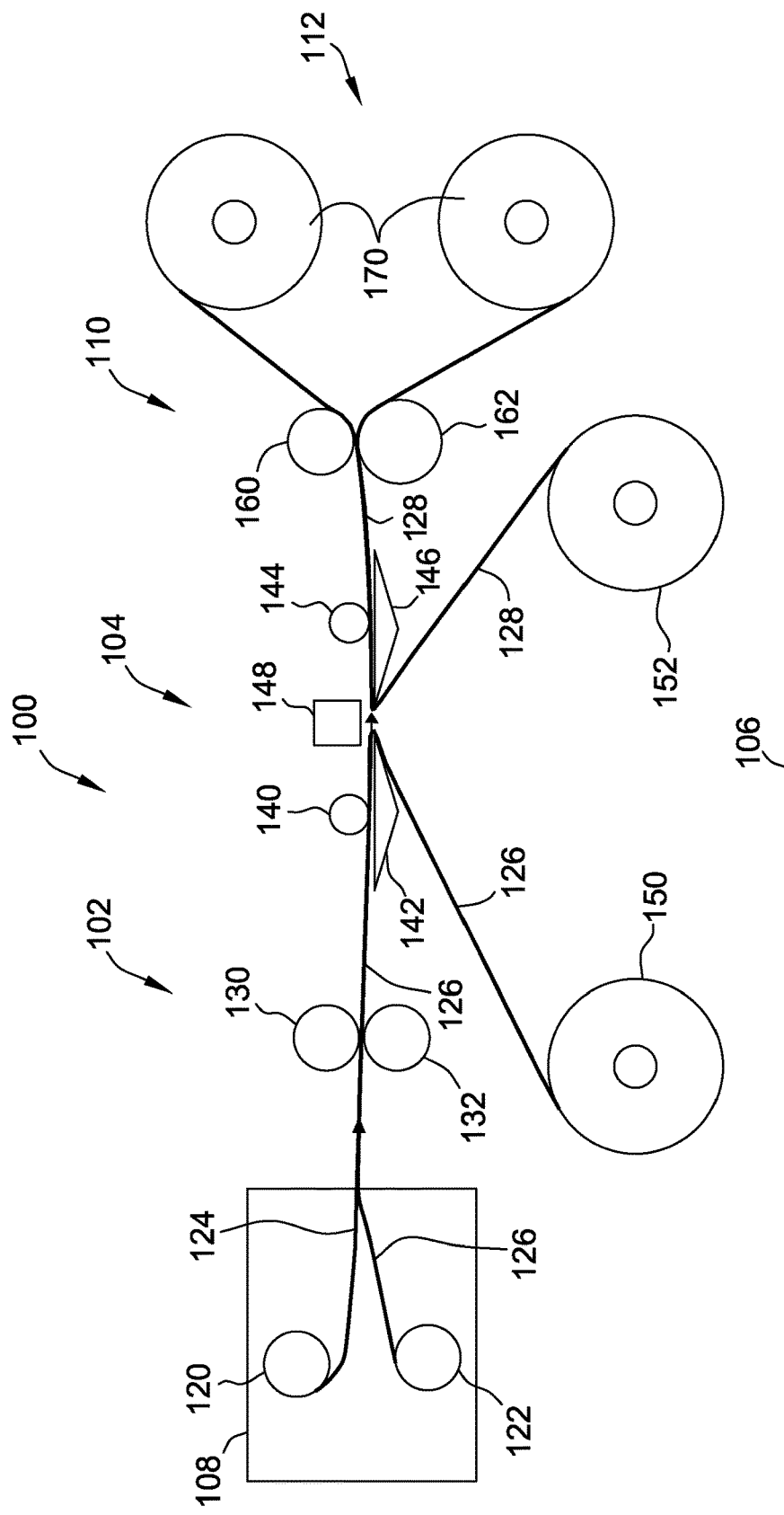
FIG. 1 is an exemplary embodiment of an assembly for preparing affixing tape in accordance with the present disclosure.

Referring to FIG. 1, a first exemplary embodiment of an assembly 100 is shown. The assembly 100 includes a cutting unit 102 and a transfer unit 104. The transfer unit 104 is downstream from the cutting unit 102, wherein "downstream" refers generally to a direction 106 of processing. "Upstream" is generally opposite of downstream direction 106. In the illustrated embodiment, the assembly 100 further includes a tape setting unit 108 upstream of a cutting unit 102, a slitting unit 110 downstream from the transfer unit 104, and at least one winding unit 112 downstream from the transfer unit 104. In the illustrated embodiment, the at least one winding unit 112 is downstream from the slitting unit 110.

Figure 2:
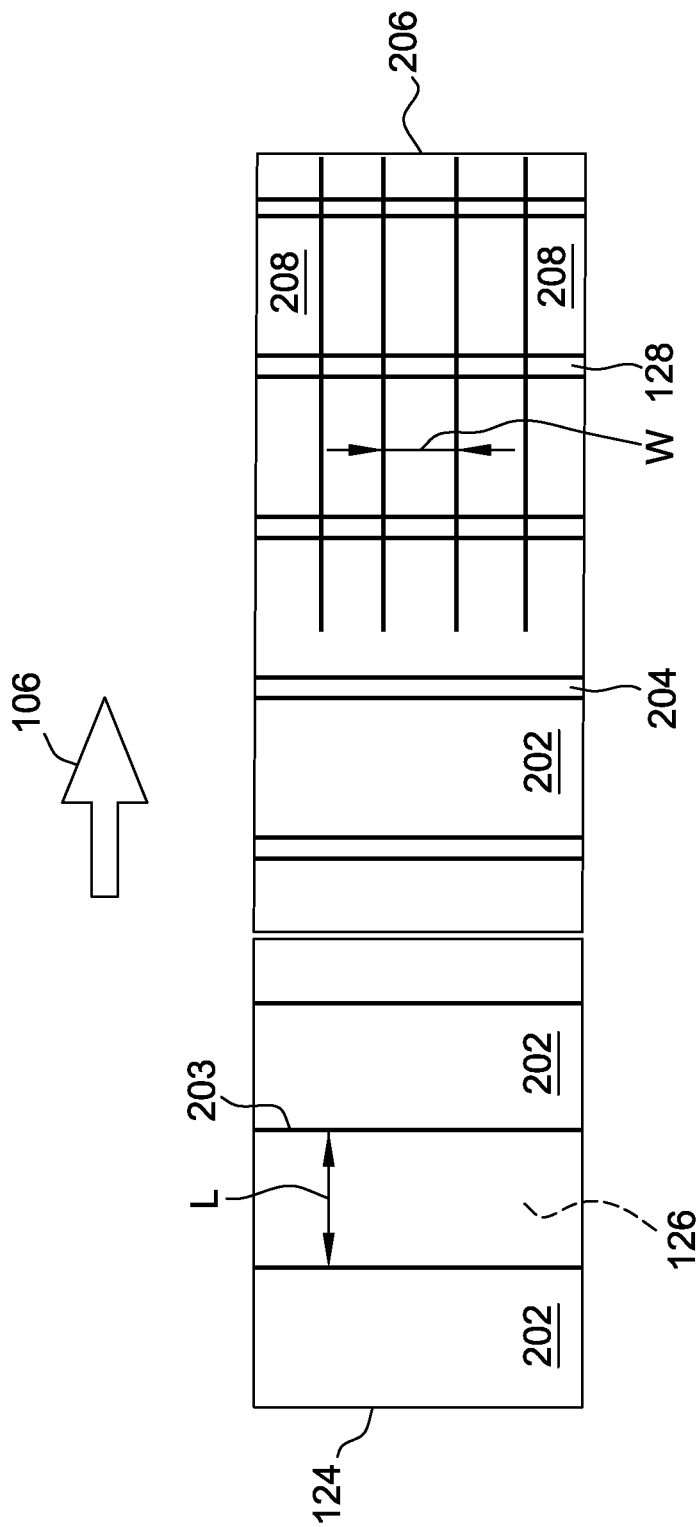
FIG. 2 is an exemplary embodiment of a cutting technique of the assembly shown in FIG. 1.

FIG. 2 illustrates the processing of the film tape 124 through the assembly 100. With reference to FIGS. 1 and 2, the downstream process through the assembly 100 is described herein.

The tape setting unit 108 includes therein at least one tape spool 120 and at least one first liner spool 122. The tape spool 120 comprises a spool or roll of differential double-coated tape (DCT) or "film tape" 124. As used herein, the phrase "film tape" refers to DCT unless indicated otherwise. More specifically, the tape spool 120 comprises a continuous band of film tape 124 wound therearound. In some embodiments, the film tape 124 has a "high-tack" adhesive on a first face and a "low-tack" adhesive on an opposing second face. The first liner spool 122 comprises a spool or roll of a first liner 126. The first liner 126 may comprise any suitable liner material, such a paper, coated paper, or polymer liner. The first liner 126 is configured to be removably coupled to the film tape 124.

The tape setting unit 108 is configured to couple the film tape 124 to the first liner 126 before cutting and further processing. In particular, the film tape 124 and the first liner 126 are coupled together upon exit from the tape setting unit 108. The tape setting unit 108 includes any internal components configured to perform such coupling, including, for example, guides, plates, actuators, presser arms, and/or any other suitable component.

The coupled film tape 124 and first liner 126 proceed to the cutting unit 102. In the illustrated embodiment, the cutting unit 102 includes a cutting cylinder 130 and a base cylinder 132. The cutting cylinder 130 is positioned adjacent the film tape 124, and the base cylinder 132 is opposite the cutting cylinder 130, adjacent the first liner 126. The base cylinder 132 acts as a guide for the coupled film tape 124 and first liner 126, as well as a cutting surface for the cutting cylinder 130. The cutting cylinder 130 includes a plurality of dies, blades, and/or any other cutting implement (not shown) suitable to cut through film tape 124. In the exemplary embodiment, the cutting implements are evenly spaced about a circumference of the cutting cylinder 130. The coupled film tape 124 and first liner 126 is drawn through the cutting unit 102 at a first speed. The cutting cylinder 130 cuts fully through the film tape 124, producing a plurality of cut pieces 202 of film tape 124. As the cutting cylinder 130 includes a plurality of evenly spaced cutting implements, the plurality of cut pieces 202 are regular or have substantially the same length L. The length L of pieces 202 is from about 0.1 in to about 10 in, or from about 0.5 in to about 5 in, or from about 1 in to about 3 in, or about 1.25 in. In the exemplary embodiment, the cutting cylinder 130 does not fully cut through the first liner 126. It should be understood that, in other embodiments, the cutting unit 102 may not have physical cutting implements but may employ alternative cutting methods, such as, for example, laser cutting methods.

In some embodiments, the cutting cylinder 130 is configured to "butt-cut" the film tape 124 into the plurality of pieces 202. A butt-cut is a single cut between adjacent pieces 202 that produces little to no waste material between pieces 202, 202. This butt-cut process may therefore save a significant amount of material, time, and cost, as no "matrix" or waste material needs to be removed. In some embodiments, the cutting unit 102 comprises a butt-cutting unit configured to cut the film tape without producing a waste material. In some embodiments, the cutting cylinder 130 is configured to cut the film tape 124 with a plurality of dies, or "die-cut" the film tape 124. In this embodiment, the die-cutting produces a waste material (not shown) between adjacent cut pieces 202. In such an embodiment, the assembly 100 further includes a waste removal unit (not shown) downstream of the cutting unit 102. The waste removal unit is configured to strip the waste material away from the first liner 126 and/or away from the plurality of cut pieces 202 of the film tape 124. In some embodiments, the plurality of cutting implements cut the pieces 202 with straight or linear edges 203. In other embodiments, the plurality of cutting implements cut the pieces 202 with any other shape of edges 203, including non-linear, curved, angled, and/or "zig-zag" edges 203. For example, cutting edges 203 with a zig-zag pattern may enable the cutting unit 102 to cut smaller pieces 202 and/or pieces 202 that are more easily removed from the first liner 126.

The first liner 126 with the plurality of cut pieces 202 thereon is drawn to the transfer unit 104. The transfer unit 104 includes a first registration component 140 and a first tension guide 142, corresponding to the first liner 126. The transfer unit 104 further includes a second registration component 144 and a second tension guide 146, corresponding to a second liner 128. The transfer unit 104 also includes a transfer component 148.

The transfer unit 104 is configured to transfer the plurality of cut pieces 202 of film tape 124 from the first liner 126 to the second liner 128. This process effectively removes any issues caused by cuts into the first liner 126, as the parts are placed on the virgin (i.e., new) second liner 128 so that no cutting has previously occurred on the second liner 128. Thus, no problems arise regarding the depth of any cut into the first liner 126. These advantages substantially, if not totally, eliminate lost production time, cost, and/or material that may be caused by cutting too deep into the first liner 126.

In the illustrated embodiment, the first registration component 140 and the first tension guide 142 cooperate to draw the first liner 126 with the plurality of cut pieces 202 thereon at the first speed through the transfer unit 104. The first tension guide 142 keeps the first liner 126 taut, and the first registration component 140 registers or identifies each cut piece 202. For example, the first registration component 140 may include a high-speed camera, scanner, light source, and/or any other suitable component. The first registration component 140 registers each cut piece 202 to track and record the placement of each cut piece 202 on the first liner 126, which enables the transfer unit 104 to monitor the speed of the first liner 126.

The second registration component 144 and the second tension guide 146 cooperate to draw the second liner 128 at a second speed through the transfer unit 104. The second speed is greater than the first speed of the first liner 126, such that the second liner 128 is moving through the transfer unit 104 faster than the first liner 126. The transfer component 148 mechanically transfers each cut piece 202 from the first liner 126 to the second liner 128. In some embodiments, the transfer component 148 is configured to perform island placements of the pieces 202 from the first liner 126 onto the second liner 128. The transfer component 148 may include any suitable components therein to transfer the pieces 202, such as, but not limited to, plates, actuators, belts, rods, wedges, levers, pulleys, etc.

In the illustrated embodiment, the transfer unit 104 further includes a liner take-up spool 150. The liner take-up spool 150 is configured to take up the "discarded" or unusable first liner 126 after the cut pieces 202 have been removed therefrom. The transfer unit 104 further includes a second liner spool 152. The second liner spool 152 comprises a spool or roll of the second liner 128. The second liner 128 may comprise any suitable liner material, such as paper, coated paper, or polymer liner. The second liner 128 may be fabricated from the same material as the first liner 126 or a different material than the first liner 126.

The second liner 128 is drawn up into the transfer unit 104 at the second speed, and the cut pieces 202 of film tape 124 are coupled to the second liner 128. In the exemplary embodiment, because the second liner 128 is moving faster than the first liner 126, the cut pieces 202 are coupled to the second liner 128 with a gap 204 therebetween. More specifically, the cut pieces 202 are coupled to the second liner 128 with an equal gap 204 between each adjacent cut piece 202. The gap 204 measures from about 0.01 in to about 1 in, or from about 0.05 in to about 0.75 in, or from about 0.1 in to about 0.5 in, or about 0.125 in.

The second tension guide 146 keeps the second liner 128 taut to receive the cut pieces 202, and the second registration component 144 registers each piece 202 on the second liner 128. The registration component 144 registers each piece 202 to track and record the placement of (e.g., the gap 204 between) each cut piece 202 on the second liner 128.

The second liner 128 with the cut pieces 202 coupled thereto is drawn to the slitting unit 110. In the illustrated embodiment, the slitting unit 110 includes a slitting cylinder 160 and a base cylinder 162. The slitting cylinder 160 is positioned adjacent the cut pieces 202 of film tape 124, and the base cylinder 162 is opposite the slitting cylinder 160, adjacent the second liner 128. The base cylinder 162 acts as a guide to move the second liner 128 through the slitting unit 110, as well as a cutting surface for the slitting cylinder 160. The slitting cylinder 160 includes a plurality of dies, blades, and/or any other cutting implement (not shown) suitable to cut through film tape 124 and the second liner 128. In some embodiments, the cutting implements are evenly spaced axially along the slitting cylinder 160. In another embodiment, the cutting implements are unevenly spaced axially along the slitting cylinder 160.

In some embodiments, the slitting unit is configured to longitudinally slit the film tape pieces 202 and the second liner 128 into a plurality of continuous strips 206. The second liner 128 is drawn through the slitting unit 110 at a first speed. The slitting cylinder 160 cuts fully through the pieces 202 of film tape 124, as well as through the second liner 128, producing a plurality of strips 206 of film tape 124 and second liner 128. In embodiments in which the slitting cylinder 160 includes a plurality of evenly spaced cutting implements, the plurality of strips 206 are regular or have substantially the same width W. The width W of the strips 206 is from about 0.1 in to about 2 in, or from about 0.25 in to about 1 in, or about 0.75 in. In embodiments in which the slitting cylinder 160 includes a plurality of unevenly spaced cutting implements, the plurality of strips 206 have varying widths W. The width W of the strips 206 is from about 0.1 in to about 2 in, or from about 0.25 in to about 1 in, or about 0.75 in. Each strip 206 includes sub-pieces 208 of film tape 124 separated by the gaps 204 and coupled to corresponding strips of the second liner 128.

Figure 3:
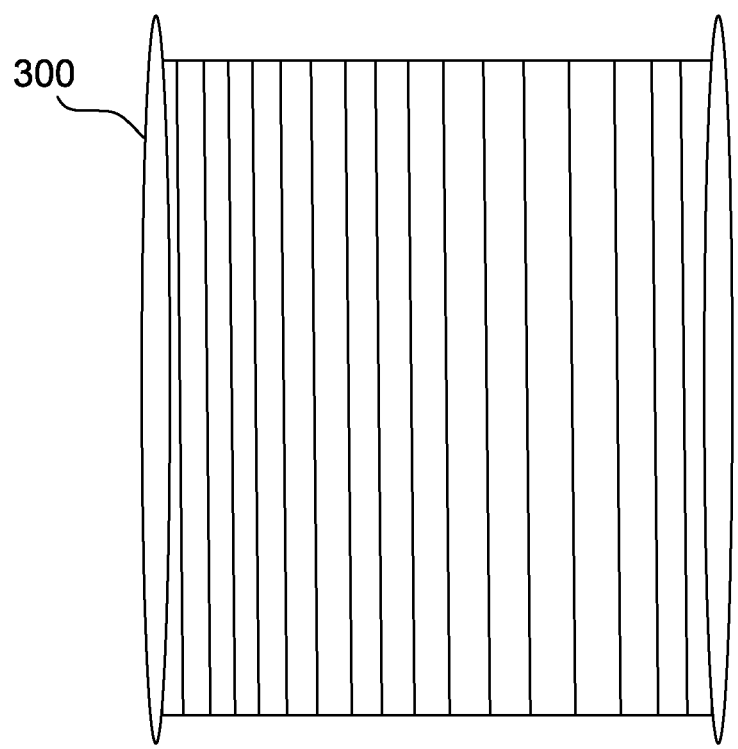
FIG. 3 is an exemplary embodiment of a wound roll prepared by the assembly shown in FIG. 1.

Each strip 206 is drawn into one winding unit 112. Each winding unit 112 includes a take-up spool 170 configured to wind at least one strip 206 thereon. In some embodiments, at least one winding unit 112 is configured to wind and spool the plurality of continuous strips 206 into at least one spooled, wound roll. In particular, each winding unit 112 is configured to wind at least one strip 206 around the take-up spool 170. Moreover, the winding unit 112 "spools" or traverse-winds the at least one strip 206 back and forth across a face (not shown) of the take-up spool 170, which allows the take-up spool 170 to hold a greater length of the strips 206 of film tape 124. Each winding unit 112 produces a corresponding wound roll 300 from the strip(s) 206. FIG. 3 illustrates one exemplary embodiment of a wound roll 300. In some embodiments, the winding unit 112 may further include a third liner spool (not shown), such that the winding unit is configured to couple a third liner (e.g., third liner 410, shown in FIG. 4) to each strip 206 before the strip 206 is wound onto the take-up spool 170. The third liner 410 is provided such that the sub-pieces 208 of film tape 124 do not decouple from the second liner 128 when the wound roll 300 is unwound.

The wound rolls 300 are provided in lengths that are at least about 5 times the length of traditional single- or self-wound rolls. In other embodiments, the wound rolls 300 are provided in lengths that are at least about 10 times the length of traditional single- or self-wound rolls. The wound roll 300 is then configured to be unspooled for use in an affixing assembly process, described herein with respect to FIG. 4.

The present disclosure is also directed to a process for preparing the film tape 124. In some embodiment, the process includes butt-cutting (e.g., using cutting unit 102) a film tape (e.g., the film tape 124) at regular intervals into pieces (e.g., pieces 202); and transferring (e.g., using transfer unit 104) the film tape pieces from a first liner (e.g., first liner 126) to a second liner (e.g., second liner 128). In some embodiments, the process includes die-cutting a film tape at intervals into pieces; and transferring the film tape pieces from a first liner to a second liner.

In some embodiments, the film tape is butt-cut and the butt-cut pieces are transferred from a first liner to a second liner to spread the pieces apart. The butt-cut pieces and the second liner coupled thereto are then slit and rolled up into wound rolls. The butt-cutting and transfer of the differential double-coated film tape to a new liner substantially eliminates any failures caused by cutting the first liner too deep.

Figure 4:
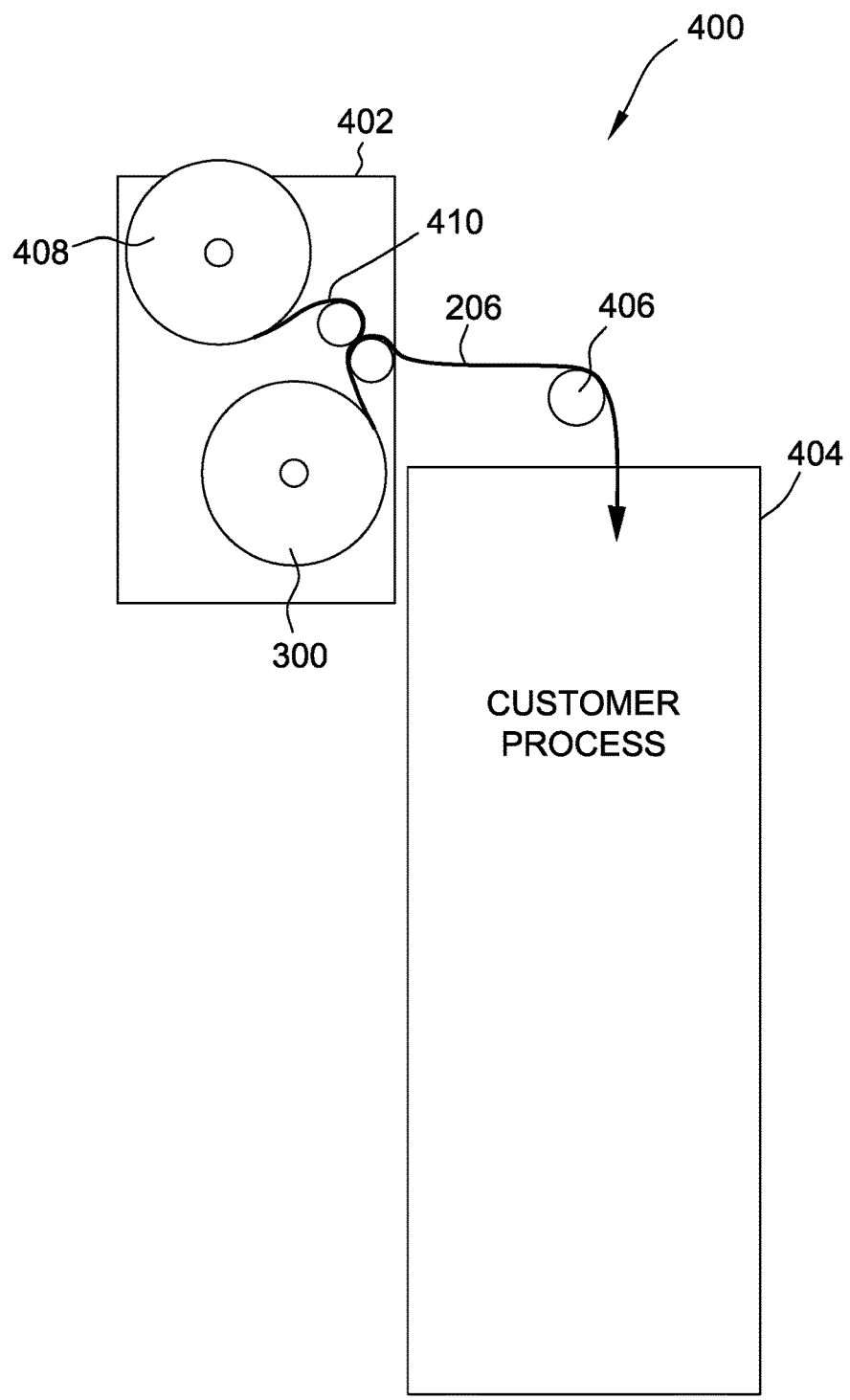
FIG. 4 is an exemplary embodiment of a retrofit assembly for using the wound roll in FIG. 3 in an affixing assembly.

Referring now to FIG. 4, an exemplary affixing assembly 400 in accordance with the present disclosure is shown. The affixing assembly 400 includes a retrofit unit 402 and a customer process unit 404. The customer process unit 404 is where the sub-pieces 208 (shown in FIG. 2) of film tape 124 are affixed to a material (not shown). The retrofit unit 402 is configured to attach or couple to the (existing) customer process unit 404 in order to make use of the wound rolls 300 (shown in FIG. 3) of film tape 124. The retrofit unit 402 includes a wound roll 300. The retrofit unit 402 is configured to unwind the strip 206 (shown in FIG. 2) from the wound roll 300. In some embodiments, the retrofit unit 402 includes servo-driven unwind components to unwind the strip 206. Where the wound roll 300 includes traverse-wound strips 206, the retrofit unit 402 "traverse-unwinds" the strips 206.

The retrofit unit 402 further includes a constant-tension direction guide 406, configured to guide the strip 206 into the customer process unit 404. In the illustrated embodiment, the direction guide 406 causes the strip 206 to travel through a 90° turn to ensure proper placement into the customer process unit 404 despite the "traverse-unwinding" of the strip 206. In the illustrated embodiment, the retrofit unit 402 further includes a constant-tension liner take-up spool 408, configured to take up the third liner 410 from the strips 206 such that the sub-pieces 208 of film tape 124 are accessible to the customer process unit 404.

The customer process unit 404 is configured to use the sub-pieces 208 of film tape 124 to affix an object to a material. In the exemplary embodiment, providing the gap 204 between adjacent sub-pieces 208 on the strip 206 allows affixing equipment of the customer process unit 404 to register or identify the gap 204 and/or sub-piece 208, to see that the gap 204 and/or sub-piece 208 is present. The affixing equipment may then affix the sub-piece 208 as designed. In some embodiments, the material to which a sub-piece 208 of film tape 124 is affixed is a mailing piece. The mailing piece is defined herein as a material that is mailed to an individual. In some embodiments, cards and/or other objects may be affixed to mailing pieces.

In some embodiments, the retrofit unit 402 includes or is coupled to the assembly 100 (shown in FIG. 1) such that the entire process of cutting, transferring, slitting, winding, and unwinding is performed "in-line". In other embodiments, the retrofit unit 402 includes one or more individual components of the assembly 100. For example, in some embodiments, a cutting unit 102 is included in the retrofit unit 402. The cutting unit 102 comprises a die-cutting unit, such that the film tape 124 may be die-cut by the cutting unit 102 "in-line" with the customer process unit 404. The cutting unit 102 alternatively comprises a butt-cutting unit, in embodiments in which the film tape 124 has a suitable width W without needing to slit the film tape into strips. When used "in-line" with the affixing customer processes, this process substantially eliminates prior industry failures caused by cutting too deep into a liner (e.g., the first liner 126) coupled to the film tape 124, because an operator of the affixing assembly 400 assembly can make adjustments on press to change the depth of the cut. Moreover, as the time between die-cutting and affixing the film tape 124 on, for example, a mailing piece is only a few seconds, this in-line process eliminates the ability of an adhesive to "flow" into the crevices of the affixing equipment and cause issues and/or failure within the affixing process. In some of these embodiments, the retrofit unit 402 or the customer process unit 404 includes a waste removal unit (not shown) to remove waste material from the die-cutting process.

The assembly and process of the present disclosure offer several advantages, including both time and procedural advantages. For example, providing a wound roll with a greater length than used in the industry allows for fewer, if any, process shut-downs during a typical work shift (e.g., 8-10 hour shift). This, in turn, allows the affixing customer process units to run longer and thus allows for significantly increased production within the same time frame.

Moreover, the butt-cut/die-cut and transferred film tape parts and/or die-cut/butt-cut in-line film tape parts substantially eliminate the possibility of any adhesive to flow into crevices cut into the liner that generally cause issues or failure of the assembly process including, but not limited to, sticking, jamming or liner breaks.

As a result, the present disclosure provides for an effective process for affixing, for example, cards to mailing pieces that runs longer, faster and with fewer production issues compared to processes currently being using in the industry.

Figure 5:
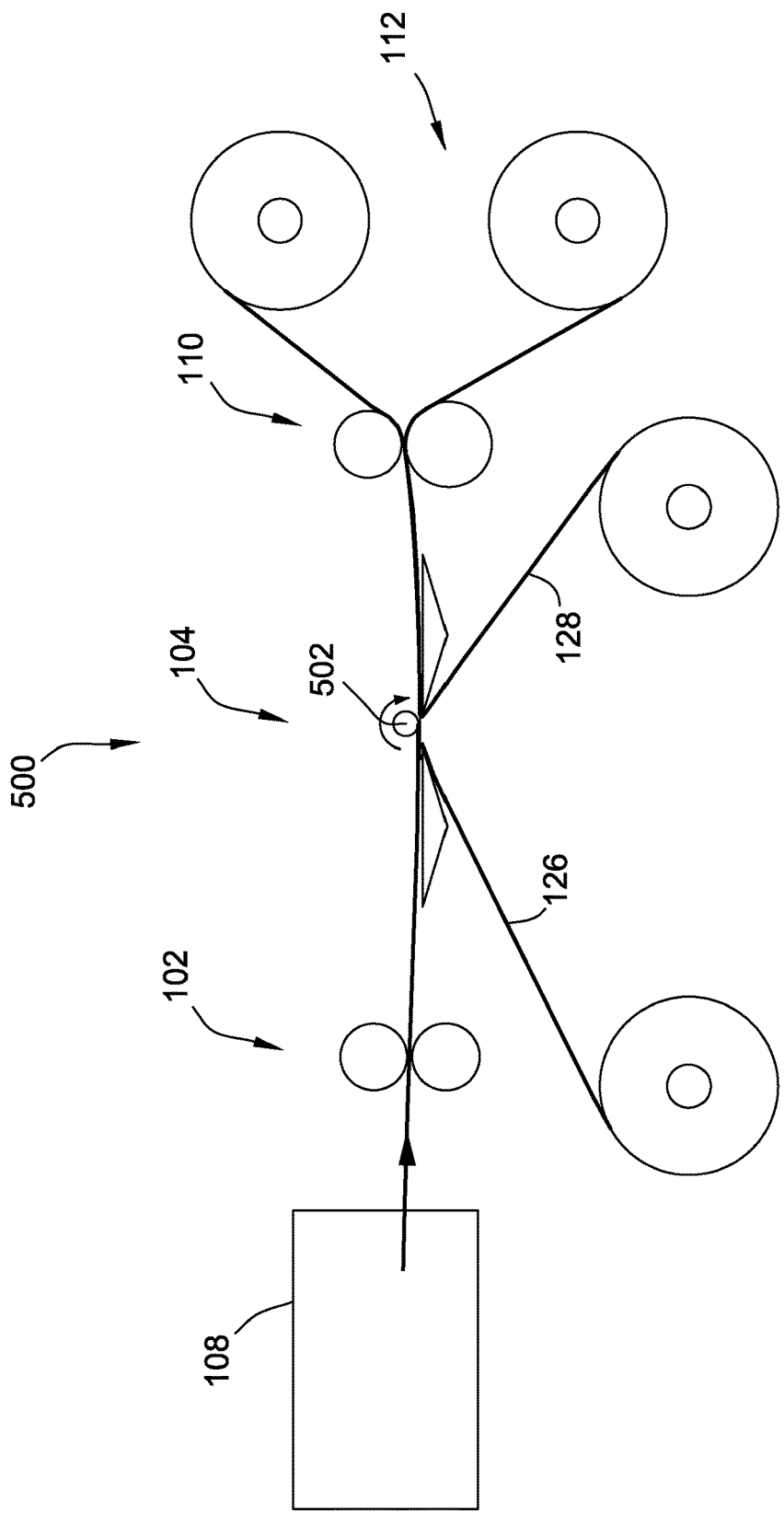
FIG. 5 is a second exemplary embodiment of an assembly for preparing affixing tape in accordance with the present disclosure.

With reference now to FIG. 5, one exemplary alternative embodiment of an assembly 500 is illustrated. In this embodiment, assembly 500 is similar to assembly 100, in that assembly 500 also includes a cutting unit 102, a transfer unit 104, a tape setting unit 108, a slitting unit 110, and winding units 112. In this embodiment, however, transfer unit 104 does not include registration components. Transfer unit 104 includes a vacuum transfer unit 502 configured to vacuum transfer at least one film tape piece 202 (shown in FIG. 2) of film tape 124 (shown in FIGS. 1 and 2) from the first liner 126 to the second liner 128 (both also shown in FIGS. 1 and 2).

When introducing elements of the present disclosure or the embodiment(s) thereof, the articles "a", "an", "the" and "said" are intended to mean that there are one or more of the elements. The terms "comprising", "including" and "having" are intended to be inclusive and mean that there may be additional elements other than the listed elements. Like references in the figures indicate like elements, unless otherwise indicated.

As various changes could be made in the above without departing from the scope of the disclosure, it is intended that all matter contained in the above description and shown in the accompanying drawings shall be interpreted as illustrative and not in a limiting sense.

What is claimed is:

1. A process comprising:
   butt-cutting a film tape at regular intervals into pieces;
   transferring the film tape pieces from a first liner to a second liner using a single transfer unit; and
   subsequently, longitudinally slitting the film tape pieces and the second liner into a plurality of continuous strips.

2. The process of claim 1, further comprising moving the second liner at a speed faster than a speed of the first liner such that the film tape pieces are transferred to the second liner with a gap therebetween.

3. The process of claim 1, further comprising winding and spooling the plurality of continuous strips into at least one spooled, wound roll.

4. The process of claim 1, wherein transferring the film tape pieces comprises vacuum transferring at least one film tape piece to the second liner.

5. The process of claim 1, further comprising coupling the film tape to the first liner before cutting.

6. A process comprising:
   die-cutting a film tape at intervals into pieces;
   transferring the film tape pieces from a first liner to a second liner using a single transfer unit; and
   subsequently, longitudinally slitting the film tape pieces and the second liner into a plurality of continuous strips.

7. The process of claim 6, wherein the die-cutting produces a waste material, the process further comprising stripping the waste material.

8. The process of claim 6, further comprising moving the second liner at a speed faster than a speed of the first liner such that the film tape pieces are transferred to the second liner with a gap therebetween.

9. The process of claim 6, further comprising winding and spooling the plurality of continuous strips into at least one spooled, wound roll.

10. The process of claim 6, wherein transferring the film tape pieces comprises vacuum transferring at least one film tape piece to the second liner.

* * * * *